United States Patent [19]

Peterson

[11] 4,310,758
[45] Jan. 12, 1982

[54] METHOD FOR EVALUATING MOISTURE TENSIONS OF SOILS USING SPECTRAL DATA

[75] Inventor: John B. Peterson, West Lafayette, Ind.

[73] Assignee: Purdue Research Foundation, West Lafayette, Ind.

[21] Appl. No.: 139,027

[22] Filed: Apr. 10, 1980

[51] Int. Cl.³ ............................ G01V 5/00; G01J 1/00
[52] U.S. Cl. ........................................ 250/255; 250/339
[58] Field of Search ............... 250/253, 255, 308, 338, 250/339, 358 R

[56] References Cited

U.S. PATENT DOCUMENTS

| | | | |
|---|---|---|---|
| 3,524,062 | 8/1970 | Rocoplan et al. | 250/358 R |
| 3,532,883 | 10/1970 | Dresia et al. | 250/358 R |
| 4,146,788 | 3/1979 | Mirkin et al. | 250/253 |

Primary Examiner—Alfred E. Smith
Assistant Examiner—Janice A. Howell
Attorney, Agent, or Firm—John R. Nesbitt; Robert E. Harris

[57] ABSTRACT

A method is disclosed which permits evaluation of soil moisture utilizing remote sensing. Spectral measurements at a plurality of different wavelengths are taken with respect to sample soils and the bidirectional reflectance factor (BRF) measurements produced are submitted to regression analysis for development therefrom of predictable equations calculated for orderly relationships. Soil of unknown reflective and unknown soil moisture tension is thereafter analyzed for bidirectional reflectance and the resulting data utilized to determine the soil moisture tension of the soil as well as providing a prediction as to the bidirectional reflectance of the soil at other moisture tensions.

23 Claims, 5 Drawing Figures

METHOD FOR EVALUATING MOISTURE TENSIONS OF SOILS USING SPECTRAL DATA

ORIGIN OF THE INVENTION

The invention described herein was made in the performance of work under a NASA grant and is subject to the provision of Section 305 of the National Aeronautics and Space Act of 1958, Public Law 85-568 (72 Stat. 435:42 U.S.C. 2457).

BACKGROUND OF THE INVENTION

Technology already exists which permits the measurement of spectral radiant power from the earth's surface. Systems carried by an aircraft or orbiting satellite are used with great success in making determination of all sorts of earth conditions, one center for this work being at the Laboratory for Applications of Remote Sensing (LARS) at Purdue University, West Lafayette, Ind.

One useful function of remote sensing is to predict world crop conditions. One important parameter in making such a prediction is the determination of soil wetness in certain major agricultural regions of the world.

In the past, these soil wetness determinations have commonly been made on a gross basis based on soil color, but it was not thought that there was any good correlation between color and wetness such that accurate determinations could be effectively made by remote sensing.

At the present time, measurement of soil water in the field depends upon sampling a given location, both in area and depth of soil profile, at a given time or times. These samples are then used to estimate the water condition of an entire area. There is no known method, however, for rapidly analyzing a large number of samples over a large area as is possible using the method of this invention (which includes establishing spectral curves for the soils in question to facilitate rapid analysis). In fact, utilizing this invention, a continuous reading across a landscape could be achieved with an electromagnetic sensor of suitable type mounted on a satellite, aircraft, or even on a ground vehicle.

Soil moisture measurements have heretofore been aimed at two soil water variables; the soil moisture content and the magnitude of the soil water potential, which is the negative of the work that must be done to remove a unit amount of the relatively loosely held soil water.

Tension, however, is the most important soil water property as far as plant behavior is concerned. Most plants suffer from lack of sufficient oxygen in the root zone when the tension is less than ⅓ Bar (field capacity) and cannot take water into their roots from surfaces of soil particles at tensions higher than 15 Bar (wilting point). Since tension depends mainly on water film thickness on particle surfaces, measurements of tension do not vary with changes in water content due to changes in the total area of the wetted surface. Hence, moisture tensions do not vary with soil texture or structure as does water content. Because of this, measurements of tension do not change with soil texture and thus are a convenient and precise way of characterizing the soil moisture regime for many practical purposes. Thus the method of this invention, which provides a rapid and accurate way of estimating soil moisture tensions, is of practical value.

Methods for measuring soil moisture are either direct or indirect. Direct methods normally call for taking samples of soil and estimating the amount of water per unit weight or volume of that soil. A sample of moist soil is dried at 105°-110° C. and reweighed when cool. Shortcomings are that the method is laborious and time consuming. Samples of field soils must be brought in airtight containers to a laboratory where balances and an oven are available. Also, in studying moisture changes in field soils, samples need to be taken at frequent intervals and at each time the new values are needed because of changes caused by precipitation, evaporation, etc. Furthermore, it is hard to tell whether the loss is due to oxidation of organic matter or to drying. Consequently, efforts have been aimed at standardizing procedures to give reproducible results rather than absolute, unequivocal values. With forced air, ten hours are usually required for drying, while with only convection currents, twenty-four hours are usually required for drying.

Modifications have been suggested to improve or speed up the drying method. One method is to mix calcium carbide with the soil water to cause the water to react to form acetylene gas which evaporates. The moisture is then determined by weight difference. This method, while rapid, is not an accurate or satisfactory method. Freeze drying has also been used. In this method, the sample is frozen, the water allowed to sublimate, and drying is continued after most of the water is removed. This method, however, calls for several operations and calls for standardizing of time and temperature to get reproducible results.

Another method proposed for speeding drying is through partial removal of water from soil samples with alcohol. After evaporation, the alcohol is burned. Results approximate those of oven drying after several treatments and burnings. This method, however, is not accurate for high organic matter soils and generally is not as accurate as the standard oven drying method.

Infrared drying has also been used but does not provide for high precision. Here again, a sample has to be brought to a laboratory and carefully prepared and treated with a standardized technique. Water can also be removed by centrifuging the wet soil sample.

For years, attempts have been made to devise an indirect method for determining soil moisture content quickly and without removing a sample from the natural situation. All these methods have resulted, however, in some disturbance of the natural condition when the apparatus is installed and are limited to the site of the installation. In addition, these methods have proven to be difficult because of the influence of soil texture and structure and of the soil solution. Hysteresis, the greater energy status which exists for soil moisture as the soil is drying compared to when it is being wetted, has also been a problem.

The basic technique heretofore commonly utilized has been to use a porous absorber which comes to equilibrium with the soil moisture. The conductance between two electrodes placed in the ground and measured by some form of Wheatstone bridge has been proposed, and without interfering factors, the conductivity varies with moisture content. In actual practice, however, changes in content of soluble salts and the difficulty of securing good contacts between electrodes and soil have been found to cause errors.

A gypsum block cast around two electrodes has also been proposed. Such a block can be buried in the soil at any depth. More recently, a unit composed of a nylon fabric encased in perforated metal and containing two electrodes has been developed.

A tensiometer has also been developed for measuring the force by which water is held in the soil expressed in terms of centimeters in height of a column of water required to produce a force of equal magnitude. The tensiometer consists of a porous clay cup attached to a mercury manometer. Tensiometers have to be set up at definite positions but once installed provide a ready reading of the tension of the soil moisture within a limited range. The highest reading possible, however, is less than one atmosphere (approximately 1000 cm. of water). The relation between soil suction and water content is not single-valued, but is influenced by soil texture and structure. Generally, however, it is not deemed necessary to interpret soil water tension in terms of moisture content for the reasons brought out hereinabove.

Soil tensions can also be measured using a centrifuge, but as with air drying techniques, this requires bringing samples to the laboratory for special preparation and treatment.

Electrical and thermal conductivity and electrical capacitance have also been studied. Unfortunately, such measurements made directly in soil have not resulted in unique correlations with water content and hence have not come into general use. Variance results from uncertain contact between electrodes and the soil as well as soil heterogeneity.

Neutron absorption or neutron attenuation has not been widely used to determine moisture content because it is limited to locations near reactors. Also the equipment must be heavily shielded. The shielded neutron probe must be lowered into an aluminum or steel tube which was previously placed in the soil. Since this method has little effect on soil moisture content, it can be used repeatedly. It cannot be used effectively, however, on small volumes of soil.

Gamma ray attenuation techniques are not limited with respect to location, but the equipment is expensive and requires shielding and other safety features. This method needs a definite set up but once installed is precise when the soil has a constant bulk density. The soil, however, must be disturbed and moved to the laboratory. The method has been used in research on water movement in soils. A disadvantage is that to be used to measure absolute moisture constants, each soil to be studied has to be calibrated.

SUMMARY OF THE INVENTION

This invention provides a novel method for evaluation of soil moisture and it is particularly well suited for remote sensing. Spectral data is collected with respect to a sample and the data utilized to establish the relationship between spectral values and moisture tension values, which relationship is then used to evaluate either the change in reflectance of soil which occurs due to changes in moisture tension or the moisture tension of the soil itself.

It is therefore an object of this invention to evaluate soil moisture, and particularly soil moisture tension, by means of remote sensing.

It is another object of this invention to evaluate the change of reflectance of soil which occurs due to changes in moisture tension and/or to evaluate the moisture tension of soil based upon collected spectral properties.

It is still another object of this invention to provide a novel method of evaluating soil moisture which includes collecting spectral data and utilizing said data to establish the relationship between spectral values and moisture tension values, which relationship is then utilized along with spectral data from a selected soil to evaluate soil moisture with respect to the selected soil.

With these and other objects in view, which will become apparent to one skilled in the art as the description proceeds, this invention resides in the novel method substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate the invention according to the best mode so far devised for the practical application of the method, and in which.

DESCRIPTION OF THE INVENTION

The method of this invention for evaluating soil moisture from spectral data and for using spectral data to predict changes in soil reflectance at different moisture tensions is based on using contemporary sensing equipment, such as the Exotech Model 20C spectroradiometer to determine spectral properties of a population of soils over a predetermined range of moisture tensions. These data are then used to develop predictive equations for evaluating expected changes in soil reflectance at different moisture tensions or the soil moisture tension from the spectral properties. While such relationships have heretofore been considered to be random, it has been found that they are, in fact, linear and predictable.

Linearity and predictability have been established by collecting an array of ratios of the reflectances of oven dry over those for ⅓ Bar water levels at 0.708 $\mu$M of surface samples of 15 Indiana soils, 11 mollisols and four alfisols of which the mollisols (prairie soils) are darker colored by Munsell color standards and significantly higher in organic carbons than the alfisols (hard-wood forest soils). This array shows two significantly different populations for the two groups by the T test basd on the ratios of the reflectances at oven dry over those at ⅓ Bar. These mean ratios are 2.89 for the mollisols and 2.2 for the alfisols.

Figure 1:
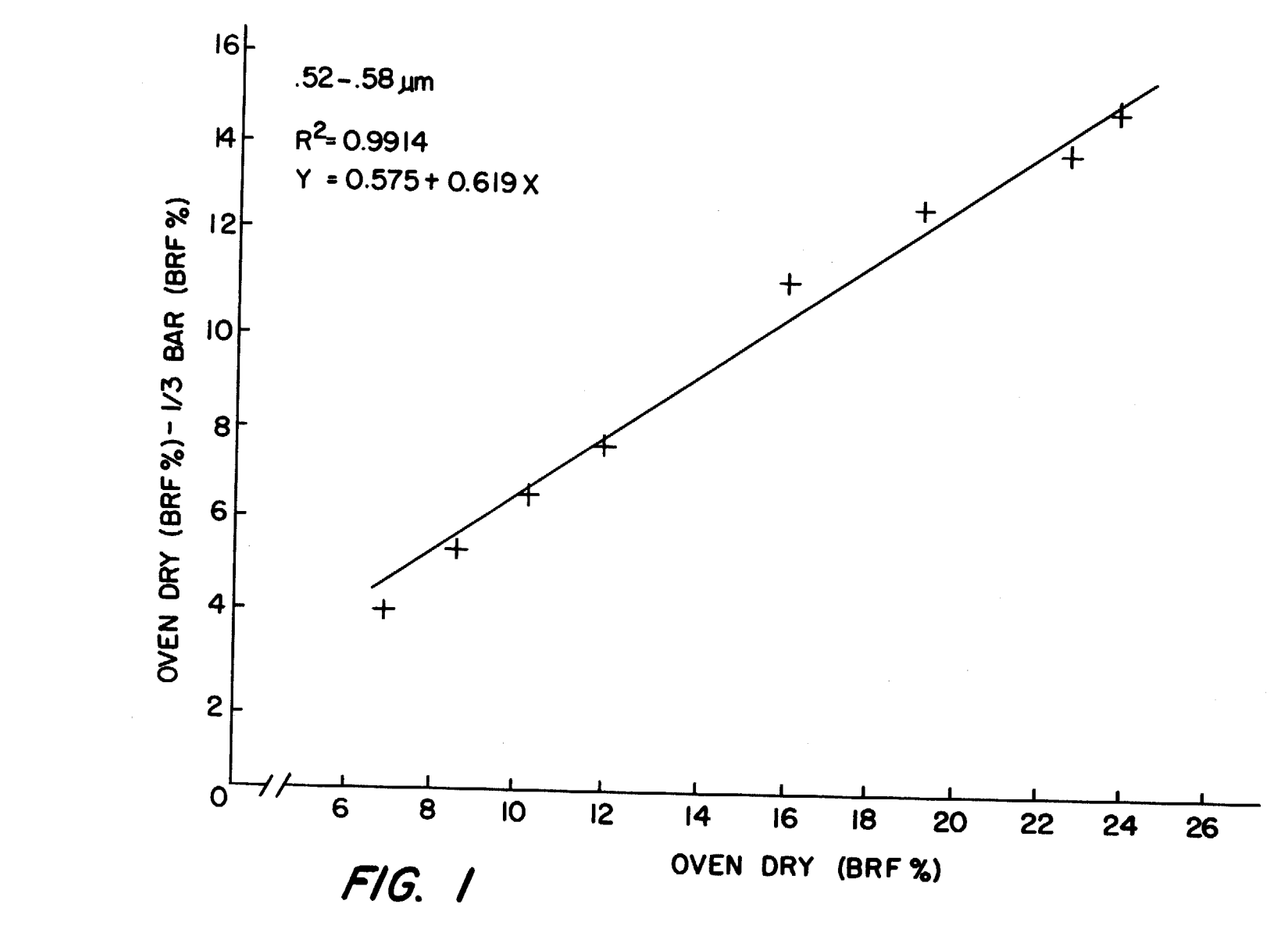
FIGS. 1 through 5 are graphs illustrating regression lines and equations for differences in reflectance of soils at oven dry versus ⅓ Bar moisture tensions at different defined wavelength bands.
Figure 2:
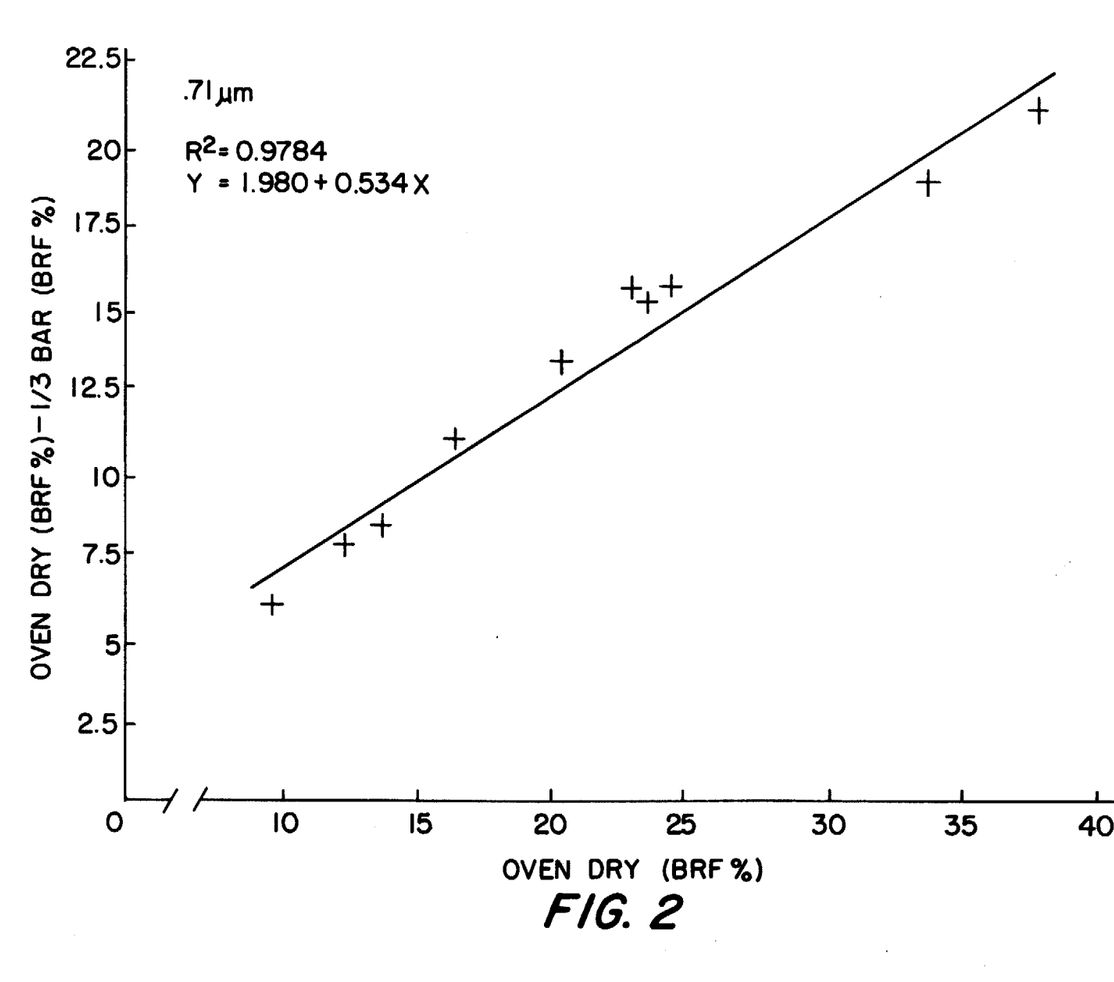

When the decrease in reflectance at 0.52 to 0.58 $\mu$M resulting from wetness (⅓ Bar reflectance—oven dry reflectance) was evaluated over the entire 15 samples, the regression shows an $R^2$ of 0.99 (FIG. 1). The $R^2$ for the loss in reflectance at 0.71 $\mu$ on wetting to ⅓ Bar versus the reflectances when oven dry is 0.98 (FIG. 2).

Figure 3:
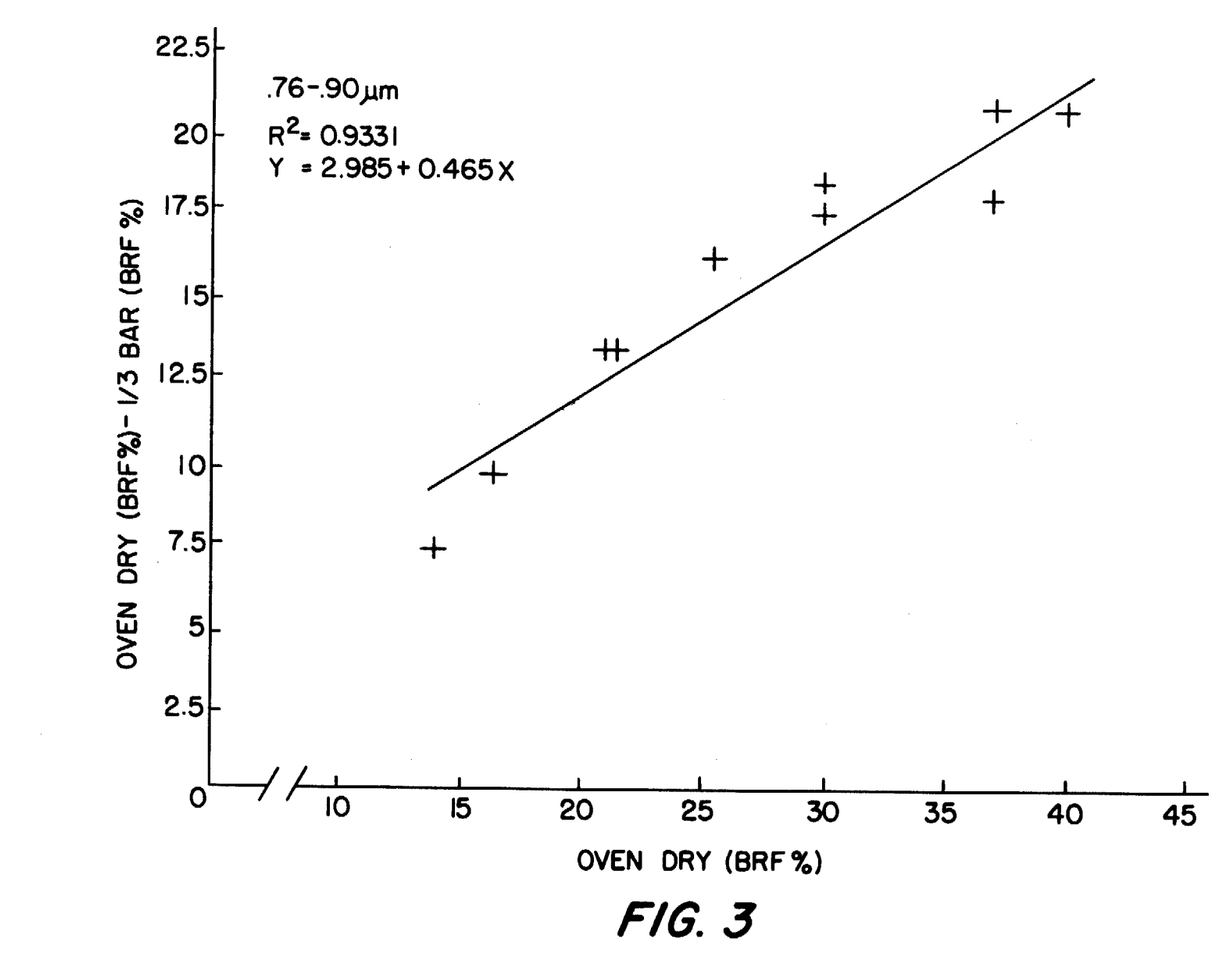
Figure 4:
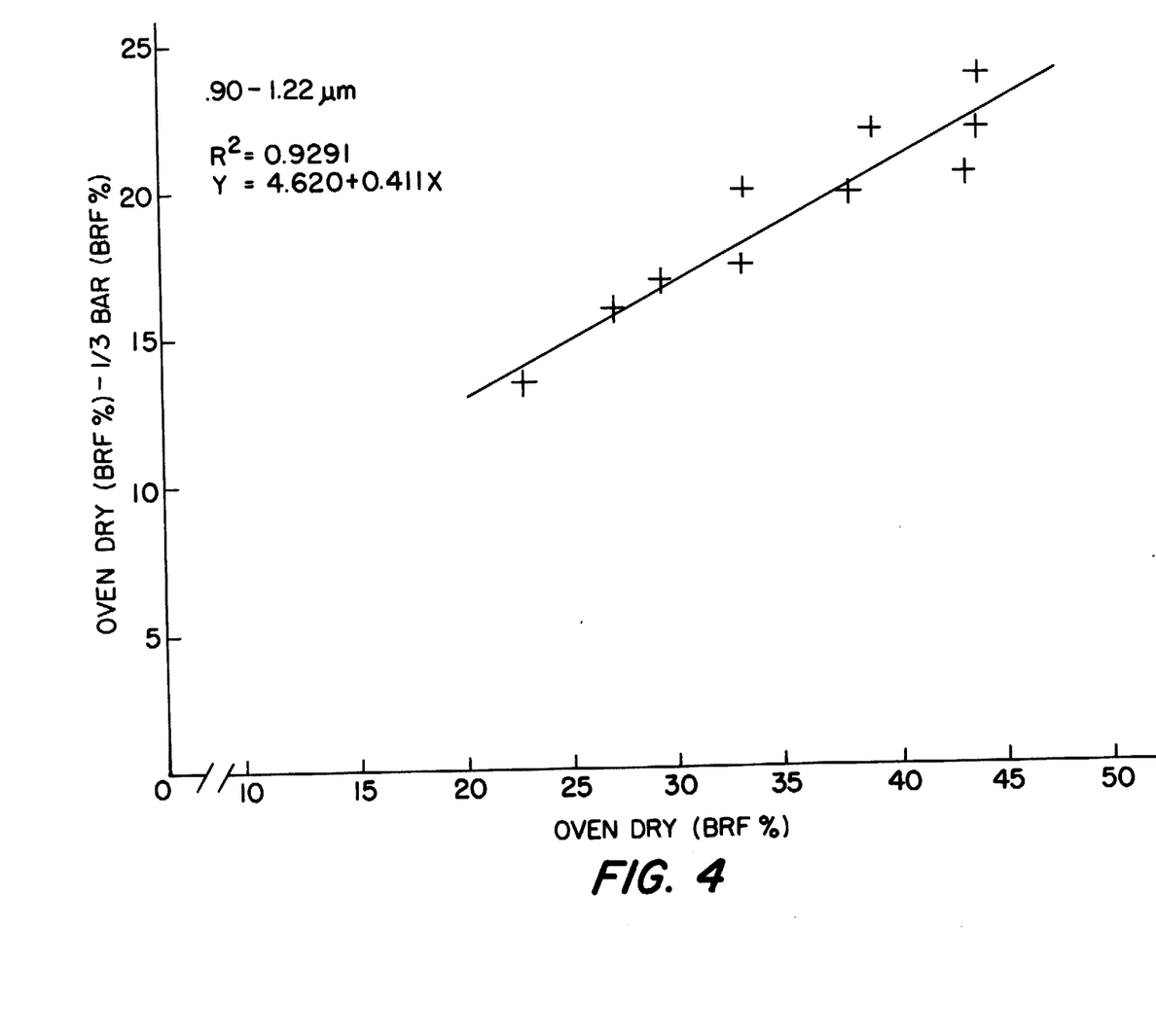
Figure 5:
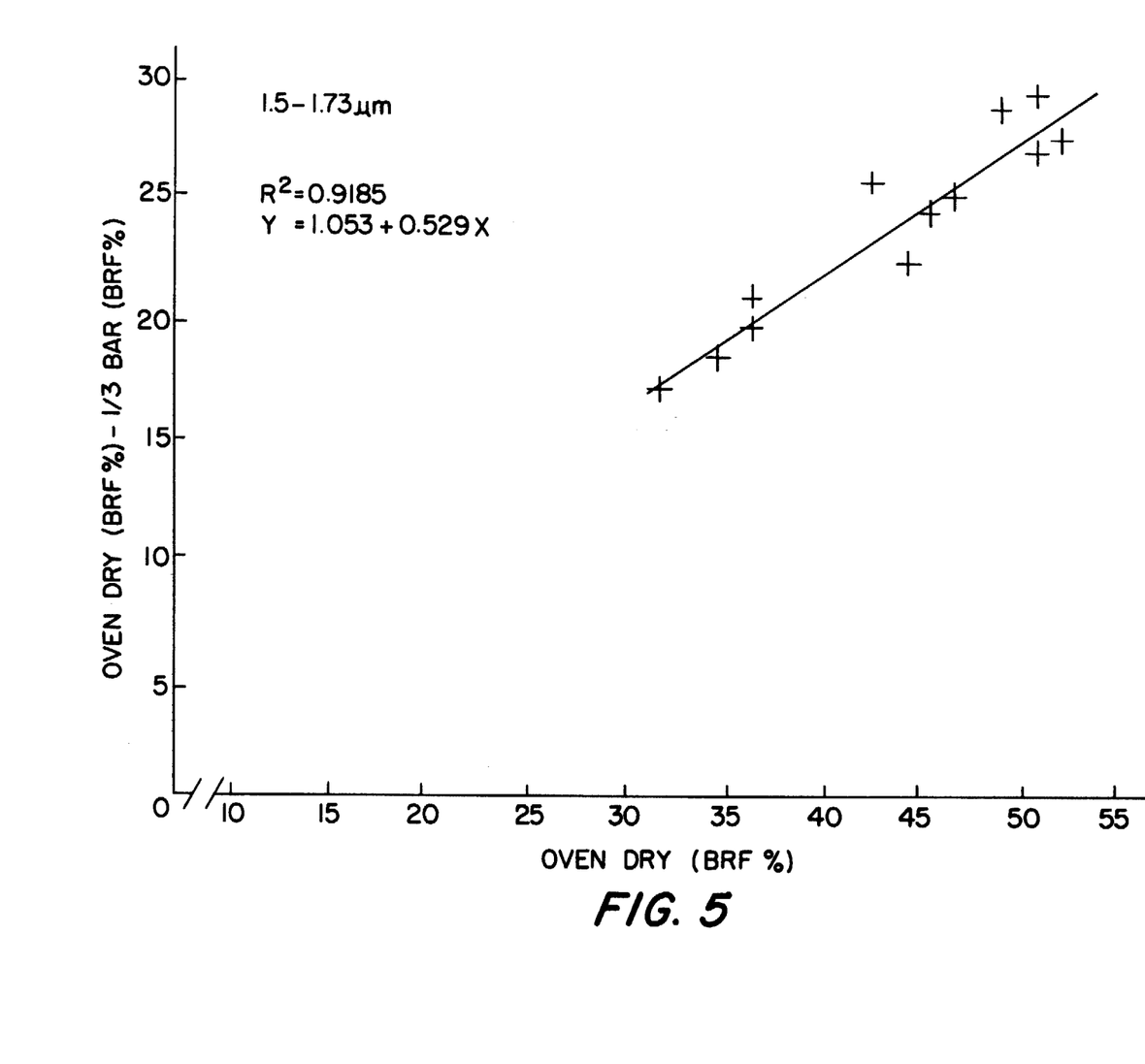

When another reflectance band is used 0.76 to 0.90 $\mu$m), a similarly orderly relationship is apparent for all 15 samples in the reduction in reflectance on increasing the moisture levels from oven dry to ⅓ Bar, in this case an $R^2$ of 0.93 (FIG. 3). Similar results were obtained for wavelength bands of 0.90 to 1.22 and 1.5 to 1.73 $\mu$m (FIGS. 4 and 5, respectively).

From the foregoing, it is therefore felt indicated that a careful analysis over a larger sample of soils will show an orderly relationship in change of reflectance among different levels of wetness. This can be expected to be systematic enough to make possible close predictions of soil moisture tensions from reflectance data and conversely of reflectance values from soil moisture data, if not for the entire population of identifiable soils, at least for subsets of that population.

Furthermore, striking evidence of the predictability of soil moisture tensions from reflectance data has been noted when the regression curves were run for the reflectance values of the 15 soils at 15 Bar and ⅓ Bar against their reflectances when oven dry. When the reflectances at 15 Bar were plotted against those of the same samples when oven dry, an $R^2$ of 0.95 was found. The equation for predicting the reflectances at 15 Bar from the reflectance values when oven dry was found to be:

$$15 \text{ Bar} = 01.685 + 1.067 \text{ oven dry}$$

Similarly, when data for reflectance of the 15 soils at ⅓ Bar were plotted against the oven dry reflectances, an $R^2$ of 0.96 was computed and the formula for estimating reflectances of the samples at ⅓ Bar on the basis of their oven dry reflectance was:

$$\tfrac{1}{3} \text{ Bar} = 0.709 + 0.487 \text{ oven dry}$$

This supports the thesis that moisture tensions of soils can be predicted from reflectance measurements.

Thus, as shown by the graphs of FIGS. 1 through 5, the plotted regression lines have been found to be quite linear for differences in reflectances of soils at oven dry versus ⅓ Bar moisture tensions at five different wavelength bands.

Reflectance is expressed as the bidirectional reflectance factor (BRF). This factor may be defined as the ratio of the reflected radiance from the target of interest to that of a reflectance standard (such as, for example, a barium sulfate powder tablet), under identical conditions of illumination and viewing. The observation parameters consist of the polar and azimuthal angles of illumination and viewing.

With respect to linear regression and $R^2$ as used herein, and given a set of data points $\{x_i, y_i, i = 1, 2, \ldots n\}$, a linear regression fits the equation $$y = ax + b$$

to the set where $$a = \left( \frac{\sum_{i=1}^{n} y_i}{n} - b \frac{\sum_{i=1}^{n} x_i}{n} \right)$$

$$b = \left( \frac{\sum_{i=1}^{n} x_i y_i - \frac{\sum_{i=1}^{n} x_i \sum_{i=1}^{n} y_i}{n}}{\sum_{i=1}^{n} x_i^2 - \frac{\left(\sum_{i=1}^{n} x_i\right)^2}{n}} \right)$$

and $$R^2 = \frac{\left( \sum_{i=1}^{n} x_i y_i - \frac{\sum_{i=1}^{n} x_i \sum_{i=1}^{n} y_i}{n} \right)^2}{\left( \sum_{i=1}^{n} x_i^2 - \frac{\left(\sum_{i=1}^{n} x_i\right)^2}{n} \right) \left( \sum_{i=1}^{n} y_i^2 - \frac{\left(\sum_{i=1}^{n} y_i\right)^2}{n} \right)}$$

$R^2$ is the coefficient of determination that measures the quality of fit of $y = ax + b$ to the data. $0 \leq R^2 \leq 1$ and the higher the value the better the quality of fit.

Steps that have been utilized in the procedure are as follows:

(a) For a population of soils to be studied, predictive equations are developed from regression curves for the relation of spectral values of soils to their soil moisture tension values.

Spectral measurements are taken with a spectral sensing device such as the Exotech Model 20C field spectroradiometer. Data are in the form of bidirectional reflectance factor (BRF) measurements taken in 0.01 μm intervals from 0.4 to 2.4 μm as collected by the Exotech Model 20C field spectroradiometer. Spectral data and auxiliary soil information are stored in digital tape for access and analysis. Good results were obtained utilizing spectral band widths of 0.52 to 0.58, 0.71, 0.76 to 0.90, 0.90 to 1.22 and 1.5 to 1.73 (as shown by FIGS. 1 through 5, respectively). (1) For the soils in the area to be studied, such as a geographic region, farm or field, representative soils are sampled. The soils are air dried, sieved through a 2 mm screen in as natural a state as possible. Each sample is then subsampled using a sample splitter, such as a Cenco soil sample splitter. Each sample is then placed in plastic rings 2 cm deep and 10 cm in diameter with filter paper on the bottom.

(2) The soil samples are saturated with water for 24 hours and equilibrated at 48 hour intervals at four moisture tensions, 1/10 Bar, ⅓ Bar, 15 Bar and oven dry (and/or other tensions as deemed necessary). Equilibration for the 1/10 and ⅓ Bar tensions is accomplished by placing the samples in their rings on a pressure plate. For higher tensions up to 15 Bar samples are equilibrated on a pressure membrane apparatus. The oven dry set is prepared by drying for 48 hours in a forced-air drying oven at 105° C.

(3) After the soils have been brought to the desired moisture tensions, they are spectrally analyzed for BRF values.

(4) Data is then submitted to regression analysis to determine whether the regressions of reflectances at one moisture tension versus those at another moisture tension over the range of samples are significant and thus may be indicative of predictable relations, if not for the whole range of soils used to establish the curves, at least for subsets for one population. Where the regression curves indicate orderly relationships, predictive equations are calculated from the data.

(b) Once the relationships have been established, a soil sample of unknown BRF and unknown soil moisture tension may be analyzed for BRF and from these data the soil moisture tension of the sample is determined and the BRF of the sample at other moisture tensions is predicted.

The foregoing shows that there are orderly shifts in reflectance values with changes in moisture tensions in soils and, for the first time, teaches a method for quantification of soil wetness based on such shifts. Computer programs are available for processing and analyzing data from the Exotech Model 20C spectroradiometer, LARSPEC; and for data from the Landsat satellite, LARSYS. From the foregoing, it can also be appreciated that rapid evaluation of moisture tension of soils can be established not only with data secured by the Exotech Model 20C spectroradiometer or modifications of the same, but also with satellite data, for example.

This invention thus provides a novel method for rapid and accurate evaluation of soil moisture by establishing the relationship between spectral values and moisture tension values for samples and then using the established relationship to determine the moisture content of a soil to be analyzed, as well as to predict changes of soil color with changes in moisture tension.

What is claimed is:

1. A method for evaluating soil moisture tension, said method comprising:
   obtaining soil samples;
   establishing from said samples the relationships between spectral reflectance values and moisture tension values for said soil samples;
   selecting soil having similarities to that of said soil samples for evaluation of moisture tension therein;
   determining spectral reflectance values for said selected soil; and
   using said determined spectral reflectance values and said established relationships between said values to evaluate soil moisture tension with respect to said selected soil.

2. The method of claim 1 wherein said spectral reflectance values for said selected soil are remotely determined.

3. The method of claim 1 wherein said spectral reflectance values are measured by a spectral sensing device producing bidirectional reflectance factor output measurements.

4. The method of claim 3 wherein said samples are equilibrated at different known moisture tensions, and wherein said measurements are taken at a plurality of different wavelengths for each of said moisture tensions.

5. The method of claim 4 wherein said output measurements are submitted to regression analysis.

6. The method of claim 5 wherein predictive equations are calculated for orderly relationships determined by said regression analysis.

7. The method of claim 1 wherein said determined spectral reflectance values and said established relationships are used to determine the moisture tension of said selected soil.

8. The method of claim 1 wherein said determined spectral reflectance values and said established relationships are used to predict the spectral reflectance values of said selected soil at other moisture tensions.

9. A method for enabling evaluation of soil moisture tension, said method comprising:
   obtaining samples of soils;
   making spectral measurements of said soil samples at a plurality of wavelengths and moisture tensions to provide bidirectional reflectance output measurements indicative thereof; and
   using said bidirectional reflectance output measurements to establish the relationship of spectral reflectance values to moisture tension for the soils sampled to thereby enable soil having similarities to that of said soil samples to be evaluated with respect to soil moisture.

10. The method of claim 9 wherein said bidirectional reflectance output measurements are submitted to regression analysis and predictive equations thereafter calculated from said regression analysis for orderly relationships.

11. An indirect method for evaluating soil moisture tension, said method comprising:
    obtaining samples of soils;
    preparing said soil samples for equilibrating at different predetermined moisture tensions;
    making spectral measurements of said prepared soil samples at predetermined different wavelengths;
    submitting said spectral measurements to regression analysis;
    developing predictive equations based upon said regression analysis;
    making remote spectral measurements of soil having similarlities to said soil samples; and
    using said equations and said remotely made spectral measurements to evaluate soil moisture tension with respect to said soil from which said remote spectral measurements were made.

12. The method of claim 11 wherein said soil samples are equilibrated at four different moisture tensions of 1/10 Bar, ⅓ Bar, 15 Bar and oven dry.

13. The method of claim 11 wherein said spectral measurements are made at five different sets of wavelengths of 0.52–0.58 $\mu$m, 0.71 $\mu$m, 0.76–0.90 $\mu$m, 0.90–1.22 $\mu$m, and 1.5–1.73 $\mu$m.

14. The method of claim 11 wherein said spectral measurements of said prepared soil samples are digitized for utilization in regression analysis.

15. The method of claim 11 wherein said equations and remotely made spectral measurements are used to quickly and accurately determine the moisture tension of the soil from which said remote spectral measurements were made.

16. The method of claim 11 wherein said equations and remotely made spectral measurements are used to quickly and accurately predict other spectral reflectance values for different moisture tensions of the soil from which said remote spectral measurements were made.

17. An indirect method for evaluating soil moisture tension, said method comprising:
    obtaining soil samples;
    saturating said samples in water;
    equilibrating said samples at a plurality of different moisture tensions;
    spectrally analyzing said samples at said plurality of different moisture tensions to provide bidirectional reflectance factor values at a plurality of different wavelengths;
    submitting said bidirectional reflectance factor values to regression analysis and determining therefrom orderly relationships;
    calibrating predictive equations from regression analysis indicative of orderly relationships;
    selecting soil having similarities to said samples and having unknown bidirectional reflectance factor values and unknown moisture tension values;
    taking remote spectral measurements of said selected soil; and determining from said remote spectral measurements and said calculated equations the soil moisture tension of said selected soil.

18. The method of claim 17 wherein said remote spectral measurements and said calculated equations are utilized to predict other bidirectional reflectance factor values and moisture tension values for said selected soil.

19. The method of claim 17 wherein said obtained samples are air dried and split prior to being saturated with water, and wherein said samples are saturated with water by saturation of said samples for 24 hours prior to being equilibrated at 48 hours intervals.

20. The method of claim 19 wherein said water saturated samples are equilibrated at four different moisture tensions of 1/10 Bar, ⅓ Bar, 15 Bar and oven dry, and wherein said spectral measurements are taken at five sets of different wavelengths of 0.52–0.58 $\mu$m, 0.71 $\mu$m, 0.76–0.90 $\mu$m, 0.90–1.22 $\mu$m, and 1.5–1.73 $\mu$m.

21. The method of claim 17 wherein said soil samples include soil indicative of at least one subset of one population of soils, and wherein said selected soil has similarities to at least said one subset of said one population of soils.

22. A method for evaluating the moisture tension of a substance having moisture adsorbing capability, said method comprising:
- obtaining samples of said substance having moisture adsorbing capability;
- establishing from said samples the relationships between spectral reflectance values and moisture tension values for said samples;
- selecting a substance having similarities to that of said samples for evaluation of moisture tension therein;
- determining spectral reflectance values for said selected substance; and
- using said determined spectral reflectance values and said established relationships between said values to evaluate moisture tension with respect to said selected substance.

23. The method of claim 22 wherein said samples are equilibrated at different moisture tensions, wherein said measurements are taken at a plurality of different wavelengths for each of said moisture tensions, and wherein said output measurements are submitted to regression analysis.

* * * * *